United States Patent [19]
Gordon

[11] 3,939,145
[45] Feb. 17, 1976

[54] NOVEL ETHEREALLY MONOSUBSTITUTED MONOSACCHARIDES

[75] Inventor: Paul Gordon, Chicago, Ill.

[73] Assignee: Strategic Medical Research Corporation, Chicago, Ill.

[22] Filed: Mar. 1, 1973

[21] Appl. No.: 337,134

[52] U.S. Cl....... 260/210 R; 260/209 R; 260/211 R; 424/180
[51] Int. Cl.² ........................................... C07H 5/06
[58] Field of Search ........ 260/209 R, 210 R, 211 R, 260/234 R

[56] References Cited
UNITED STATES PATENTS

| 2,374,236 | 4/1945 | Salzberg et al.................. | 260/211 R |
| 2,785,152 | 3/1957 | Jonas ............................. | 260/210 R |
| 3,723,617 | 3/1973 | Sutton............................. | 260/210 R |

Primary Examiner—Johnnie R. Brown
Attorney, Agent, or Firm—L. S. Van Landingham, Jr.

[57] ABSTRACT

The invention provides a novel therapeutic composition comprising a pharmaceutically acceptable carrier containing a therapeutically effective amount of an ethereally monosubstituted monosaccharide having the general formula S-O-Y, wherein S is the residue of a monosaccharide selected from the group consisting of pentoses, hexoses and heptoses and Y is selected from the group consisting of cyclic monovalent nitrogen containing organic radicals and residua and monovalent organic radicals and residua having the general formula

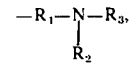

wherein $R_1$ is a divalent organic radical having a linear carbon chain length of about 1–7 carbon atoms and $R_2$ and $R_3$ are selected from the group consisting of —H, —OH, —SH, halogen and monovalent organic radicals and residua having a linear carbon chain length of about 1–7 carbon atoms. The invention also provides certain novel ethereally monosubstituted monosaccharides, of which 3-O-3'-(N',N'-dimethylamino-n-propyl)-D-glucose is an example. The novel monosaccharides show striking antiviral activity or other therapeutically valuable properties and are useful as an active ingredient in the above therapeutic composition. The invention further provides a method of therapeutically treating warm blooded animals with the aforementioned therapeutic composition and novel monosubstituted monosaccharides.

24 Claims, No Drawings

NOVEL ETHEREALLY MONOSUBSTITUTED MONOSACCHARIDES

BACKGROUND OF THE INVENTION

The present invention is concerned with a novel therapeutic composition and a method of therapeutically treating warm blooded animals therewith. In one of its more specific variants, the invention further relates to certain novel ethereally monosubstituted monosaccharides which are especially useful as ingredients in the aforementioned composition and in practicing the aforementioned method.

Many diseases caused by certain living micro-organisms may be treated very effectively by administering a therapeutically effective amount of an antibiotic. However, antibiotics are not effective in the treatment of virus infections insofar as suppressing the proliferation of the virus particles and reducing cell damage are concerned.

A number of substances other than antibiotics have been proposed heretofore for use in treating virus infections, but they have not been used extensively for a number of reasons. For instance, the previously proposed antiviral agents usually exhibit very low antiviral activity and have little positive effect on the course of the viral infection. The previously proposed antiviral drugs also have not been effective in the treatment of a wide spectrum of virus infections and this has been a major disadvantage. The therapeutic treatment of a large number of patients having undetermined viral infections of widely differing types is impractical with the narrow spectrum prior art antiviral drugs as it is too difficult to determine the exact virus causing the infection and then select an effective drug. Many potentially effective antiviral drugs are toxic and can not be safely administered to patients, and still other antiviral drugs have undesirable side effects. As a result of the foregoing and other deficiencies, it is apparent that an entirely satisfactory wide spectrum nontoxic antiviral drug has not been available heretofore for routinely administering to patients having a viral infection caused by many of the common viruses.

It has been discovered that certain ethereally monosubstituted monosaccharides provide important biological signals which allow living cells to resist virus infections. As will be described in greater detail hereinafter, the signals also provide other types of control in cell chemistry.

The therapeutic compositions of the invention overcome the disadvantages of the prior art antiviral agents noted above, and also produce other unusual and unexpected results. For example, the ethereally monosubstituted monosaccharides described hereinafter are therapeutically effective at very low concentrations while at the same time they exhibit no side effects and are very non-toxic. The ratio of the minimum toxic to therapeutic dose is greater than 50 in both tissue culture and animals.

It is an object of the present invention to provide a therapeutic composition including a pharmaceutically acceptable carrier and a therapeutically effective amount of certain ethereally monosubstituted monosaccharides to be described more fully hereinafter.

It is a further object to provide certain novel compounds to be described more fully hereinafter, which are ethereally monosubstituted monosaccharides exhibiting striking antiviral activity and/or other therapeutically valuable properties.

It is still a further object to provide a therapeutic composition containing one or more of the novel monosaccharides of the invention.

It is still a further object to provide a method of therapeutically treating a warm blooded animal wherein the above described therapeutic composition and/or novel monosaccharides are administered thereto in a therapeutically effective amount.

Still other objects and advantages of the invention will be apparent to those skilled in the art upon reference to the following detailed description.

DETAILED DESCRIPTION OF THE INVENTION INCLUDING PREFERRED VARIANTS THEREOF

The novel therapeutic composition of the invention comprises a pharmaceutically acceptable carrier and a therapeutically effective amount of an ethereally monosubstituted monosaccharide having the general formual S-O-Y and organic acid and inorganic acid salts thereof, wherein S is the residue of a monosaccharide selected from the group consisting of pentoses, hexoses and heptoses and Y is selected from the group consisting of cyclic monovalent nitrogen containing organic radicals and residua and monovalent organic radicals and residua having the general formula

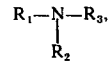

wherein $R_1$ is a divalent organic radical having a linear carbon chain length of about 1–7 carbon atoms and $R_2$ and $R_3$ are selected from the group consisting of —H, —OH, —SH, halogen and monovalent organic radicals and residua having a linear carbon chain length of about 1–7 carbon atoms. When $R_2$ or $R_3$ is halogen, the halogen may be F, Cl, Br or I, of which Cl or Br is usually preferred. The organic radical $R_1$, and $R_2$ and $R_3$ when they are organic radicals, may be branched or unbranched linear carbon chains and may be saturated or unsaturated and, when saturated, the linear and/or branched carbon chains may contain one or more double or triple carbon-to-carbon bonds. The linear and/or branched carbon chains of $R_1$, $R_2$ and $R_3$ may be substituted or unsubstituted and, when substituted, one or more substituents may be present such as —OH, —SH, halogen (F, Cl, Br and/or I), branched or unbranched and saturated or unsaturated hydrocarbon radicals containing 1–7 and preferably 1–3 carbon atoms, —$OR_4$ and/or —$SR_4$ radicals wherein $R_4$ is a branched or unbranched and saturated or unsaturated hydrocarbon radical containing 1–7 and preferably 1–3 carbon atoms, carboxylic acid residues containing 1–7 and preferably 1–3 carbon atoms, and amino groups and aminohydrocarbon radicals containing 1–7 and preferably 1–3 carbon atoms. Preferably $R_1$ is a hydrocarbon radical having a linear carbon chain length of 1–3 or 1–4 carbon atoms and $R_2$ and $R_3$ are individually selected from the group consisting of hydrogen and/or hydrocarbon radicals having linear carbon chain lengths of 1–3 or 1–4 carbon atoms.

Examples of compounds from which cyclic organic radicals and residua are derived include (a) monovalent nitrogen containing saturated, unsaturated or aromatic carbocyclic compounds containing about 4–8 carbon atoms in the ring and preferably about 5–6 carbon atoms in the ring and at least one nitrogen atom attached thereto or to an organo substituent thereon, (b) heterocyclic organic compounds containing about 3–8 carbon atoms in the ring and at least one ring nitrogen atom and (c) derivatives of the foregoing compounds wherein at least one substituent is present such as —OH, —SH, halogen (F, Cl, Br and/or I), branched or unbranched and saturated or unsaturated hydrocarbon radicals containing 1–7 and preferably 1–3 carbon atoms, —$OR_5$ and/or —$SR_5$ radicals wherein $R_5$ is a branched or unbranched and saturated or unsaturated hydrocarbon radical containing 1–7 and preferably 1–3 carbon atoms, carbocyclic acid residues containing 1–7 and preferably 1–3 carbon atoms, and amino groups and aminohydrocarbon radicals containing 1–7 and preferably 1–3 carbon atoms.

The monosaccharide residue S may exist in an open chain or cyclic form. However, it is usually preferred that the ethereally monosubstituted monosaccharide have the following general formula:

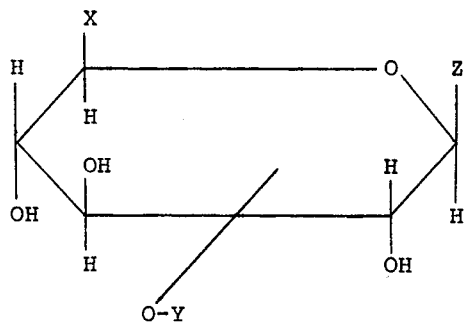

wherein X and Z are H, OH and/or hydroxyalkyl groups containing up to 2 carbon atoms and Y represents the same organic radicals and residua as aforementioned for the general formula S-O-Y. The above general formula illustrates the hexacyclic form of the various isomers of the pentoses, hexoses and heptoses, the relative spatial configuration of the -H and -OH groups about the ring, and the monosubstitution thereof in accordance with one presently preferred variant of the invention. The hydroxyl group of the hemiacetal or hemiketal linkage may assume an α or a β configuration. The compounds of the invention may be in the form of anomers or mixtures of anomers.

The configurations of the various isomers of the pentoses, hexoses and heptoses are well known to those skilled in this art and numerous reference books are available on the subject, the teachings of which are incorporated herein by reference. For example, see *Textbook of Biochemistry*, 4th Edition, by West et al. (1966); *Advanced Organic Chemistry*, by Fieser and Fieser (1961); and *Organic Chemistry*, by Paul Karrer (1947). The prior art discloses, for example, a total of eight open chain isomers for the reducing pentoses, 16 open chain isomers for the reducing hexoses, and an even larger number of open chain isomers for the reducing heptoses. One half of the aforementioned isomers have the property, when in aqueous solution, of causing a plane of polarized light to rotate to the right and thus are referred to as dextrorotatory compounds and are given the prefix D- or (+) to distinguish them from their levorotatory counterparts, which are given the prefix L- or (−). Either the D-series or the L-series of the pentoses, hexoses and heptoses may be used in practicing the invention, but it is usually preferred to use the D-series. The hexoses often give the best results and especially D-talose, D-galactose, L-galactose, D-idose, D-gulose, D-mannose, D-glucose, L-glucose, D-altrose and D-allose. The aforementioned pentoses, hexoses and heptoses may be ethereally monosubstituted in any available position. Nevertheless, it is understood that substitution of certain positions of specific monosacchardides results in more therapeutically active or less toxic compounds. For instance, substitution of the 1-O- and 3-O- positions of glucose and the 6-O- position of galactose results in especially valuable compounds.

The following substituents may be ethereally substituted on any of the available positions of the various isomers of the pentoses, hexoses and heptoses to produce nontoxic compounds having exceptional therapeutic activity:
-(n-propylamino),
-(N',N'-dimethylamino-n-propyl),
-(N',N'-dimethylaminoisopropyl),
-(N-methyl piperidyl),
-(N',N'-dimethylaminoethyl),
-(N',N'-diethylaminoethyl), and
-(2',N',N'-trimethylamino-n-propyl).

Of the foregoing substituents, -(N',N'-dimethylamino-n-propyl) is presently preferred and especially when substituted in the 1-O- or 3-O- position of glucose or in the 6-O- position of galactose.

The following compounds have been found to have exceptional wide spectrum antiviral activity and other therapeutically valuable properties and are presently preferred for use in the composition and method of the invention:
3-O-3'-(n-propylamino)-D-glucose,
3-O-3'-(N',N'-dimethylamino-n-propyl)-D-glucose,
3-O-4'-(N-methyl piperidyl)-D-glucose,
3-O-2'-(N',N'-dimethylaminoethyl)-D-glucose,
3-O-2'-(N',N'-diethylaminoethyl)-D-glucose,
3-O-3'-(2',N',N'-trimethylamino-n-propyl)-D-glucose,
α-N,N-dimethylaminoisopropyl-D-glucoside,
6-O-3'-(N',N'-dimethylamino-n-propyl)-D-galactose,
3-O-2'-(N',N'-dimethylaminopropyl)-D-glucose,
6-O-2'-(N',N',-dimethylaminopropyl)-D-galactose, and organic acid and inorganic acid salts thereof. Of the foregoing compounds, 3-O-3'-(N',N'-dimethylamino-n-propyl)-D-glucose is presently preferred.

Additional compounds of the general formula S-O-Y, wherein Y is

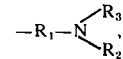

which may be used in practicing the invention are listed below:

| Monosaccharide Residue (S) | Substituent (Y) | | |
|---|---|---|---|
| | $R_1$ | $R_2$ | $R_3$ |
| 3-O-D-Glucose | 3'-n-propyl | H | methyl |
| " | " | ethyl | " |
| " | " | H | ethyl |
| " | 2'-n-propyl | methyl | methyl |
| " | 3'-1,2-propenyl | " | " |
| " | sec.-butyl | " | " |

-continued

| Monosaccharide Residue (S) | Substituent (Y) | | |
|---|---|---|---|
| " | 3'-butyl | " | " |
| " | 2'-ethyl | H | H |
| " | methyl | H | H |
| 6-O-D-Galactose | 3'-n-propyl | H | methyl |
| " | " | ethyl | " |
| " | " | H | ethyl |
| " | 3'-1,2-propenyl | methyl | methyl |
| " | sec.-butyl | " | " |
| " | 3'-butyl | " | " |

Still other compounds of the general formula S-O-Y, wherein Y is a cyclic monovalent nitrogen containing organic radical or residue, which may be used in practicing the invention are as follows:

| Monosaccharide Residue (S) | Substituent (Y) | |
|---|---|---|
| | Cyclic Radical | Substituent on the Cyclic Radical |
| 3-O-D-Glucose | 4'-piperidyl | H |
| " | 3'-piperidyl | methyl, H |
| " | 2'-piperidyl | " |
| " | 3'-pyrrolidyl | " |
| " | 2'-pyrrolidyl | " |
| 6-O-D-Galactose | 4'-piperidyl | H |
| " | 3'-piperidyl | methyl, H |
| " | 2'-piperidyl | " |
| " | 3'-pyrrolidyl | " |
| " | 2'-pyrrolidyl | " |

The present invention also provides certain novel compounds which have wide spectrum antiviral activity. The novel compounds may be defined generically as follows:
  3-O-3'-(N',N'-dimethylamino-n-propyl)-glucose,
  3-O-4'-(N-methyl piperidyl)-glucose,
  3-O-2'-(N',N'-dimethylaminoethyl)-glucose
  3-O-3'-(2',N',N'-trimethylamino-n-propyl)-glucose,
  α-N,N-dimethylaminoisopropyl-glucoside,
  6-O-3'-(N',N'-dimethylamino-n-propyl)-galactose,
  3-O-2'-(N',N'-dimethylaminopropyl)-glucose,
  6-O-2'-(N',N'-dimethylaminopropyl)-galactose, and
  organic acid and inorganic acid salts thereof.
Species of the foregoing novel compounds which possess striking wide spectrum antiviral activity are as follows: 3-O-3'-(N',N'-dimethylamino-n-propyl)-D-glucopyranose,
  3-O-4'(N-methyl piperidyl)-D-glucopyranose,
  3-O-2'-(N',N'-dimethylaminoethyl)-D-glucopyranose,
  3-O-3'-(2',N',N'-trimethylamino-n-propyl)-D-glucopyranose,
  α-N,N-dimethylaminoisopropyl-D-glucoside,
  6-O-3'-(N',N'-dimethylamino-n-propyl)-D-galactopyranose,
  3-O-2'(N',N'-dimethylaminopropyl)-D-glucopyranose,
  6-O-2'-(N',N'-dimethylaminopropyl)-D-galactopyranose, and
  organic acid and inorganic acid salts thereof.

In general, the preparation of the monosubstituted compounds described herein involves the formation of alkyl ethers or substituted alkyl ethers at selected positions on the desired monosaccharide, such as at position 1-O- or 3-O- of D-glucose, position 6-O- of D-galactose, and position 3-O- of D-fructose. The condensation of the substituent substrate with the monosaccharide at the desired position may be achieved by various prior art techniques. One method is described in U.S. Pat. No. 2,715,121, issued Aug. 9, 1955 to GLEN, et al., the disclosure of which is incorporated herein by reference. The method described in this patent requires extreme reaction conditions and often gives low yields. The product purity is also less than satisfactory.

The preferred method of preparation involves much milder reaction conditions than employed in U.S. Pat. No. 2,715,121. The side reactions are minimized, the purity of the final product is greatly improved and the method may be adapted to a series of solvents having varying properties such as tetrahydrofuran, dioxane and benzene. Briefly, the improved method involves the reaction of a monosaccharide which has been blocked with one or more organo groups in the hydroxyl group positions adjacent the desired position to be substituted. The blocked monosaccharide is dissolved in one of the foregoing solvents and is reacted with a halogenated organo amino compound having the desired carbon chain length and configuration in the presence of a base such as sodium hydroxide. The resulting intermediate products are blocked derivatives of the compounds of the invention. The blocking groups may be removed by hydrolysis and the resulting free amine may be purified to arrive at the final product, which may be in the form of a salt. Further details of this preferred method are set out in the Examples appearing hereinafter. In practicing one variant of the invention, the above mentioned blocked intermediate product may be used as an ingredient in the therapeutic composition and method of the invention. This will be described more fully below.

It is understood that simple derivatives of the compounds described herein are embraced by the invention. Such derivatives may be prepared by prior art techniques and procedures and used as an ingredient in the therapeutic composition and method of the invention.

For example, the free amine compounds are basic and form organic acid salts and inorganic acid salts, and the resulting salts are useful in the therapeutic composition and method of the invention. The salts may be prepared by the usual prior art techniques, such as by adding the free amine compound to water and then adding the desired organic acid or mineral acid thereto in an amount sufficient to neutralize the free amine. Examples of suitable acids include HCl, HBr, $H_2SO_4$, $HNO_3$, benzoic acid, p-aminobenzoic acid, p-acetamidobenzoic acid, p-hydroxybenzoic acid, alkane sulfonic acid, p-toluene sulfonic acid, acetic acid, alkyl-carboxylic acids, oxalic acid, tartaric acid, lactic acid, pyruvic acid, malic acid, succinic acid, gluconic acid and glucuronic acid. The aqueous solution of the resulting salt is evaporated to the volume necessary to assure precipitation of the salt upon cooling. The precipitated salt is recovered by filtration, washed and dried to obtain a final amine salt product. The amine salts are often preferred for use in formulating the therapeutic compositions of the invention as they are crystalline and relatively nonhygroscopic. The amine salts are also better adapted for intramuscular injection than are the free amines.

The compounds of the invention possess strong hydrophilic properties due to the presence of a plurality of free hydroxyl groups. In some instances, it is desirable to decrease the hydrophilic properties and thereby increase the solubility of the compound in the fatty tissues of a warm blooded animal to be therapeutically treated therewith. This technique also aids in the transportation of the drug to a desired tissue or the concentration thereof in a desired tissue. In practicing one variant of the invention, a labile organic substituent is selected which temporarily blocks at least one free monosaccharide hydroxyl group and thereby decreases the hydrophilic properties temporarily, and allows the compound to be transported or concentrated in fatty tissues. The labile organic substituent is removed in vivo during treatment of the warm blooded animal and the hydroxyl group is unblocked. The initial hydrophilic properties of the compound are thus restored thereby assuring its effectiveness as a drug.

Prior art blocking techniques may be employed such as acetonization and acetylation. Suitable prior art blocking methods are described in the aforementioned U.S. Pat. No. 2,715,121 and are described in the specific examples appearing hereinafter. In instances where an aldehyde or ketone is reacted with hydroxyl groups on adjacent carbon atoms, the initial compound may be dissolved in the desired aldehyde or ketone under anhydrous conditions and a Lewis acid catalyst is added in a catalytic quantity, such as 1% zinc chloride or anhydrous phosphoric acid. Often acetone is the preferred blocking agent, but aldehydes or ketones of much higher molecular weight may be used when desired such as those containing up to 25 carbon atoms. The reaction mixture is agitated at room temperature for a prolonged reaction period, such as 24–48 hours. The compound may be blocked in a plurality of positions, such as the 1,2- and 5,6- positions. It is usually preferred to block positions such as the 1,2- positions as the resulting partially blocked compound is much less toxic.

It is also possible to block one or more free hydroxyl positions of the compound with an ester group, wherein the carboxylic acid residue contains 1–18 and preferably 1–3 carbon atoms. The ester derivatives likewise may be prepared following prior art techniques such as by reacting a carboxylic acid anhydride with the compound following prior art practices. Additionally, the alpha or beta alkyl derivatives of monosaccharides such as glucose may be prepared following prior art techniques. In this later instance, the compound is dissolved in a dry alcohol having the desired carbon chain length and reacted with the compound in the presence of a catalyst such as hydrogen chloride. While the above discussed derivatives are presently preferred, it is understood that still other simple derivatives may be prepared following prior art techniques and then used in practicing the present invention. In addition to the foregoing, the compounds may also include monosubstituted monosaccharides in which the substrate

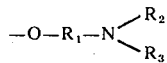

may be replaced by a substituent $R_7$, where $R_7$ is a deoxymonosaccharide derivative of halogen, keto, amino, lower alkyl, mercapto, alkenyl, alkynyl, aromatic, heterocyclic or alkylcarboxylic acid and its derivatives. $R_7$ may also represent the same groups as the above substrate of the monosaccharide ethers. Still other antiviral agents have a general formula S-O-Y wherein Y is -$R_8$-S-$R_9$, where $R_8$ is saturated or unsaturated hydrocarbon radical containing 1–7 carbon atoms and $R_9$ is a monovalent saturated or unsaturated hydrocarbon radical containing 1–7 carbon atoms or hydrogen.

The compounds of the invention are especially useful as wide spectrum antiviral agents for the therapeutic treatment of warm blooded animals. They exhibit potent antiviral activity against both RNA and DNA viruses, which is highly unusual and unexpected in view of the very limited and specific antiviral activity of the prior art antiviral agents. The compounds of the present invention exhibit marked suppression of virus particle multiplication and virus-induced cell injury in animal and human cell tissue culture systems, against such widely varying viruses as herpes simplex, influenza A and mumps. In tests in the whole animal, the compounds can reduce mortality and morbidity manifestations of influenza infections by from 50 to 85%.

The compounds of the present invention may be administered to human patient or animal to be treated either orally or by parenteral administration. When the therapeutic composition is to be administered orally, the compound may be admixed with a prior art filler and/or binder such as starch and a disintegrator, and the admixture is pressed into a tablet of a size convenient for oral administration. Capsules also may be filled with the powdered therapeutic composition and administered orally. Alternatively, a water solution or suspension of the therapeutic composition may be admixed with a flavored syrup such as cherry syrup and administered orally. When the therapeutic composition is administered by intramuscular injection, the compound is usually dissolved in a physiological saline solution which contains sodium chloride in sufficient concentration to make the overall solution to be injected isotonic to body fluids. A salt of the free amine compound is usually preferred in instances where the compound is administered by intramuscular injection. In treating upper respiratory viral infections, the salt form in aqueous solution may also be administered by nasopharyngeal spray. Administration also may be made by means of a suppository in patients unable to retain medication administered by mouth.

The dosage may be varied over extremely wide limits as the compounds are effective at low dosage levels, and are relatively free of toxicity and adverse side effects. The compounds may be administered in the minimum quantity which is therapeutically effective, and the dosage may be increased as desired up to the maximum dosage tolerated by the patient. Animal toxicity data indicate that the limiting non-toxic dosage may be up to 100-200 times the minimum effective dosage. Also, it is not necessary to carefully control the dosage for patients sensitive to the prior art antiviral drugs. As a general rule, the compound may be administered in an amount of about 1–40 milligrams per kilogram of body weight per day, and preferably in an amount of about 2–20 milligrams per kilogram per day, over the period required for treatment of the viral infection.

Surprisingly, the compounds described herein have still other unusual and unexpected therapeutically valuable properties. The learning of new tasks is enhanced. The therapeutic composition also protects against death due to water deprivation. The buffer capacity of the compounds over a pH range of approximately 7–9.8 is very good and they may be used for this purpose. Certain compounds also exhibit lubricative properties and may be used as a specialized lubricant. Compounds such as 3-O-D-glucopropionitrile are photosensitive and may be used in photographic applications.

The following specific Examples further illustrate the present invention.

EXAMPLE 1

To a solution of 104 g (0.4 mole) of 1,2:5,6-di-O-isopropylidene-D-glucofuranose in 550 ml of tetrahydrofuran (THF) was added 189.7 g (1.2 mole) of 3-chloro-N,N-dimethylamino propane in the form of the hydrochloride salt and 144 g (3.6 mole) of sodium hydroxide. The suspension was mechanically stirred and heated to reflux for 18 hours. The reaction mixture thus prepared was filtered, the solids were washed with THF, and the washings were combined with the filtered liquid. The THF was removed under reduced pressure and an amber-colored viscous oil was obtained.

The oil was distilled under high vacuum (less than 1 mm Hg) while using a very slight dry nitrogen purge to obtain high and low boiling fractions. The low boiling fraction was identified as unreacted 3-chloro-N,N-dimethylamino propane. The high boiling fraction had a boiling point of 139°–143°C at 0.07 mm Hg and was a clear viscous oil with an optical rotation of $\{\alpha\}_D^{25} = -19.3°$ neat (100 mm) and a density of 0.95 g/cc. The refractive index was $\eta_D^{26} = 1.4576$. Gas chromatography showed a purity greater than 99%. An elemental analysis showed C, H, N and O contents of 59.13%, 8.99%, 4.12% and 27.70% respectively. The yield was 80% of the novel compound 1,2:5,6-di-O-isopropylidene-3-O-3'-(N',N'-dimethylamino-n-propyl)-D-glucofuranose.

A portion of the above oil (10 g) was hydrolyzed in aqueous sulfuric acid at a pH value of 1.9–2.1 for 10 hours with refluxing. The resulting solution was adjusted to a pH value of 4.5 with saturated $Ba(OH)_2$ solution, centrifuged, and filtered through an ultrafine filter. The filtrate was lyophillized to a white to slightly yellow solid having a melting point of 78°–80°C. Gas chromatography data indicated above 99% purity of the novel compound 3-O-3'-(N',N'-dimethylamino-n-propyl)-D-glucopyranose. In thin layer chromatography, the flow rate on silica gel with a solvent mixture composed of n-propanol, ethyl acetate, $H_2O$ and $NH_3$ in the ratio by volume of 60:10:30:10 respectively, was $R_f = 0.356$.

The gas-liquid chromatograms for the above intermediate and final novel compounds were run on a Beckman G.C. Model 72 - 5 with a hydrogen flame detector. The column used for the intermediate novel compound was a commercially available SE-52 column, wherein methylphenyl resins act as stationary phases supported on Chromosorb W (H.P.), which is made by Johns-Manville Corporation. The final novel compound was chromatographed on a Chromosorb 103 glass column, which is packed with porous resins. The foregoing materials are commercially available.

EXAMPLE 2

A solution of 26.0 g of 1,2:3,4-di-O-isopropylidene-D-galactopyranose in 50 ml of anhydrous THF was mixed with a suspension of 0.3 mole of 3-chloro-N,N-dimethylamino propane hydrochloride and 36 g of sodium hydroxide in 100 ml THF. The mixture was stirred vigorously and refluxed for three hours. The resulting brownish solution was cooled, filtered and most of the solvent was evaporated leaving a brown oil. The remaining solvent and unreacted 3-chloro-N,N-dimethylamino propane were removed by fractional distillation under reduced pressure. The residual oil was extracted with chloroform, decolorized with activated charcoal and dried over anhydrous magnesium sulfate. Removal of the chloroform solvent yielded 13.4 g of yellow oil, which was identified as 1,2:3,4-di-O-isopropylidene-6-O-3'-(N',N'-dimethylamino-n-propyl)-D-galactopyranose. Infrared and gas chromatography in accordance with Example 1 indicated the presence of one major component having a refractive index of $\eta_D^{28} = 1.461$ and an optical rotation of $\{\alpha\}_D^{25} = -49.4°$ in chloroform.

The oil was refluxed with 50 ml of 0.5 N sulfuric acid for 18 hours. The resulting solution was washed with chloroform and the pH value was adjusted to 4.2. On lyophillization, the aqueous solution yielded 4.67 g of white crystalline solid 6-O-3'-(N',N'-dimethylamino-n-propyl)-D-galactopyranose having an optical rotation of $\{\alpha\}_D^{25} = +77.2°$ in $H_2O$. A gas chromatography analysis in accordance with Example 1 indicated that the purity of the product was in excess of 95%.

EXAMPLE 3

Starting with 51 g (0.3 mole) of 4-chloro-N-methylpiperidine hydrochloride, 26 g (0.1 mole) of 1,2:5,6-di-O-isopropylidene-D-glucofuranose and 36 g of NaOH in 150 ml THF, condensation was accomplished using the general procedure outlined in Example 1. The residue remaining following vacuum distillation was dissolved and recrystallized from hot methanol. The melting point was 106°–107.5°C (sharp).

Hydrolysis of the above product in $H_2SO_4$ at a pH value of 2.1 yielded 3-O-4'-(N-methylpiperidyl)-D-glucopyranose having an optical rotation of $\{\alpha\}_D^{25} = +38.42°$ in $H_2O$. A gas chromatography analysis in accordance with Example 1 indicated that the purity of the product was in excess of 96%. The melting point was 62°–65°C.

EXAMPLE 4

A solution of 0.1 mole of 1,2:5,6-di-O-isopropylidene-D-glucofuranose in 50 ml of THF was added to a suspension of 0.3 mole of 2-chloro-N,N-diethylaminoethane hydrochloride and 36 g of sodium hydroxide in 100 ml of THF. The suspension was mechanically stirred and refluxed overnight and the reaction mixture was treated as set out in Example 1. The desired product, 1,2:5,6-di-O-isopropylidene-3-O-2'-(N',N'-diethylaminoethyl)-D-glucofuranose was obtained as a clear yellow liquid (b.p. 144°–150°C/0.15 mm Hg) having an optical rotation of $\{\alpha\}_D^{28} = -20.6°$ neat and a refractive index of $\eta_D^{25} = 1.4532$. The liquid solidified on exposure to air, probably due to formation of the carbonate salt. The yield was 85%.

Ten grams of the above product were hydrolyzed with aqueous sulfuric acid at a pH value of 1.9–2.1 for ten hours under reflux. The resulting solution was adjusted to a pH value of 4–5 with saturated barium hydroxide solution and then centrifuged and filtered. Lyophillization of the filtrate yielded 6.55 g of light brown crystalline 3-O-2'-(N',N'-diethylaminoethyl)-D-glucopyranose. The optical rotation in water was $\{\alpha\}_D^{25} = +36.33°$. A gas chromatography analysis in accordance with Example 1 indicated that the purity was in excess of 99%.

EXAMPLE 5

To 26 g (0.1 mole) of 1,2:5,6-di-O-isopropylidene-D-glucofuranose and 36 g (0.9 mole) of sodium hydroxide in 150 ml of refluxing THF was added dropwise over one hour 0.3 mole of 3-bromopropionitrile in 50 ml of THF. The reaction mixture was refluxed for an additional 6 hours and then filtered. The solids were washed with THF and the washings were combined with the filtrate. The solvent was removed under reduced pressure and solid di-O-isopropylidene-3-O-3'-propionitrile-D-glucofuranose was obtained. The decomposition point was 165°C and it was light sensitive indicating utility in photographic applications.

Five grams (0.016 mole) of the above product were dissolved in anhydrous ether and added dropwise to a suspension of 0.76 g (0.02 mole) of lithium aluminum hydride in ether. The resulting complex was dissolved in cold HCl and neutralized rapidly with sodium bicarbonate. The suspension thus produced was extracted with chloroform and the solvent was removed to obtain a yellow oil in a yield of 250 mg. Gas chromatography in accordance with Example 1 indicated a purity of 98% and there was a sharp IR band at 3400 cm$^{-1}$. The oil was hydrolyzed at a pH value of 2.1 in sulfuric acid and lyophillized to dryness. The yield was 85 mg of 3-O-3'-(n-propylamino)-D-glucopyranose.

EXAMPLE 6

The 3-O-2'-(N',N'-dimethylaminopropyl) derivative of 1,2:5,6-di-O-isopropylidene-D-glucofuranose was prepared by condensing 0.1 mole of 1,2:5,6-di-O-isopropylidene-D-glucofuranose with 0.3 mole of 2-chloro-N,N-dimethylamino propane hydrochloride in the presence of 0.9 mole of sodium hydroxide in 150 ml of THF. The reaction mixture was fractionally distilled under reduced pressure to obtain a yellow viscous oil (b.p. 142°–145°C/0.07 mm Hg) in 81% yield. The optical rotation was $\{\alpha\}_D^{25} = -21.5°$ neat and the refractive index was $\eta_D^{25} = 1.4549$. Gas chromatography in accordance with Example 1 indicated only one component.

The above prepared yellow viscous oil (10 g) was hydrolyzed with aqueous sulfuric acid at a pH value of 2.0 by refluxing for 10 hours. The pH value of the hydrolysate was adjusted to 4-5 with saturated barium hydroxide solution, filtered and lyophillized to obtain 10.5 g of light yellow crystals of 3-O-2'-(N',N'-dimethylaminopropyl)-D-glucopyranose. The optical rotation in water was $\{\alpha\}_D^{25} = +37.86°$. Gas chromatography in accordance with Example 1 indicated a purity in excess of 82%.

EXAMPLE 7

α-N,N-dimethylaminoisopropyl-D-glucoside was prepared by starting with 0.1 mole of anhydrous D-glucose in 300 ml of THF and adding 0.3 mole of N,N-dimethylamino-2-propanol along with 95 g of dry Dowex 50-X cation exchange resin in H$^+$form. The reaction mixture was refluxed for 18 hours and then 70 ml of 5 N ammonium hydroxide was added. The reaction mixture was filtered and the filtrate was concentrated under reduced pressure to obtain a brown viscous oil. The oil was dissolved in hot ethanol, decolorized with charcoal, dried with anhydrous MgSO$_4$, and acidified with dry HCl gas. The ethanol solution was concentrated from 500 ml to approximately 100 ml and allowed to cool under running tap water. The α-N,N-dimethylaminoisopropyl-D-glucoside product crystallized from the concentrated solution upon scratching the container. Thin layer chromatography in accordance with Example 1 indicated a flow rate on silica gel of $R_f = 0.34$.

EXAMPLE 8

To 0.1 mole of 1,2:5,6-di-O-isopropylidene-D-glucofuranose was added 0.3 mole of 2,N,N,-trimethylaminopropyl chloride hydrochloride along with 36 g of sodium hydroxide. The general reaction procedure was in accordance with Example 1. The oil resulting from the reaction had a boiling point of 144°–146°C at 0.6mm Hg and an optical rotation of $\{\alpha\}_D^{20} = -20.05°$ neat.

The above product was hydrolyzed according to the general method outlined in Example 1 to obtain the desired 3-O-3'-(2', N',N'-trimethylamino-n-propyl)-D-glucopyranose. The optical rotation of the product in water was $\{\alpha\}_D^{20} = +38.0°$.

EXAMPLE 9

This example illustrates the preparation of 6-O-2'-(N',N'-dimethylaminopropyl)-D-galactose.

The general procedure of Example 2 was followed with the exception of using 2-chloro-N,N-dimethylaminopropane hydrochloride as a starting material rather than the corresponding 3-chloro derivative. The intermediate product had an optical rotation in water of $\{\alpha\}_D^{24} = -54.5°$, and a refractive index of $\eta_D^{24} = 1.4552$. The final product had a rate of flow value on thin layer chromatography analysis in accordance with Example 1 of $R_f = 0.376$.

EXAMPLE 10

Well established methodology of the prior art was employed to determine the antiviral potency of compounds against influenza A$_2$ virus, Hong Kong strain, in tissue cultures, employing the baby hamster kidney cell line (see R. L. Muldoon, L. Mezny and G. G. Jackson in Antimicrobial Agents and Chemotherapy 2:224–228, 1972). Virus infectivity was evaluated by both hemagglutination techniques and cytopathogenic effects, with identical results for each method. In Table 1 below, the virus-inhibiting effects of two low drug concentrations, 3 and 10 μg/ml, are depicted. Results are given as the log decrease in infectivity of the virus inoculum. A log decrease of 4.0 is the maximum obtainable, representing complete suppression of virus growth in the system. The virus inoculum of day 0 was always 100 times that amount required to kill 50% of the tissue culture cells (100 TCD$_{50}$). These results indicate that different derivatives suppress viral growth by from 3 to 10,000 fold, the most potent effect being exerted by 3-O-3'-(N',N'-dimethylamino-n-propyl)-glucose.

TABLE 1

| Compound | Log Decrease in Infectivity of Virus Inoculum at Concentration of | |
|---|---|---|
| | 3 μg/ml | 10 μg/ml |
| 3-O-3'-(N',N'-dimethylamino-n-propyl)-D-glucose | 3.2 | 4.0 (max.) |
| 3-O-4'-(N-methylpiperidyl)-D-glucose | 2.5 | 3.5 |
| 3-O-2'-(N',N'-dimethylaminoethyl)-D-glucose | 2.5 | 3.5 |
| 3-O-3'-(2',N',N'-trimethylamino-n-propyl)-D-glucose | 2.4 | 3.0 |
| α-N,N-dimethylaminoisopropyl glucoside | 1.5 | 2.5 |
| 6-O-3'-(N',N'-dimethylamino-n-propyl)-D-galactose | 1.0 | 2.0 |
| 3-O-2'-(N',N'-dimethylaminopropyl)-D-glucose | 1.0 | 2.0 |

TABLE 1-continued

| Compound | Log Decrease in Infectivity of Virus Inoculum at Concentration of | |
|---|---|---|
| 3-O-2'-(N',N'-diethylaminoethyl)-D-glucose | 0.5 | 1.0 |
| 6-O-2'-(N',N'-dimethylaminopropyl)-D-galactose | 0.1 | 0.5 |

Kong disease in mice. In this study mice were infected by a sublethal, disease-producing dose of mouse-adapted human influenza virus and were treated either with distilled water (control) or with 40 mg/Kg compound. Fifty percent of the administered drug was in a form reduced in hydrophilicity by addition of a labile organic group, i.e., acetone, to the 1,2- positions to promote absorption into the cells and slow release from body fat. Medi- Table 2

| Compound | Concentration required to exert 50% inhibition of herpes-induced plaque formation ($\mu$g/ml) | Concentration required to exert 100% inhibition of herpes-induced plaque formation ($\mu$g/ml) |
|---|---|---|
| 3-O-3'-(N',N'-dimethylamino-n-propyl)-D-glucose | 0.3 | 1 |
| 3-O-4'-(N-methylpiperidyl)-D-glucose | 0.7 | 6 |
| 6-O-3'-(N',N'-dimethylamino-n-propyl)-D-galactose | 2 | >10 |
| 3-O-3'-(2',N',N'-trimethylamino-n-propyl)-D-glucose | 2 | 7 |
| 3-O-2'-(N',N'-diethylaminoethyl)-D-glucose | 2 | 20 |
| 1,2:5,6-di-O-isopropylidene-3-O-3'-(N',N'-dimethylamino-n-propyl)-D-glucofuranose | <3 | — |
| 1,2:5,6-di-O-isopropylidene-3-O-4'-(N-methylpiperidyl)-D-glucofuranose | <3 | — |
| 3-O-2'-(N',N'-dimethylaminopropyl)-D-glucose | 3 | >20 |
| 3-O-3'-n-propylamino-D-glucose | 3 | 20 |
| 1,2:5,6-di-O-isopropylidene-3-O-2'-(N',N'-diethylaminoethyl)-D-glucofuranose | 6 | 30 |
| $\alpha$-N,N-dimethylaminoisopropyl glucoside | 10 | >50 |

EXAMPLE 11

Using well established methodology of the prior art, derivatives were examined for their capacity to inhibit the multiplication of herpes simplex virus in tissue culture. Therapeutic effects were evaluated by the plaque formation technic of Rapp (see Fred Rapp in Journal of Immunology 93:643, 1964). The concentrations of the drug required to reduce plaque formation by 50% and by 100% respectively were determined. In Table 2 below, the results given illustrate the effectiveness of a number of derivatives and high dependence of potency on drug structure. As in the influenza study, the most potent derivative is 3-O-3'-(N',N'-dimethylamino-n-propyl)-glucose. Identical anti-herpes results as given above were obtained with study of cytopathogenic effects, whether in primary rabbit kidney or human embryo cell tissue culture lines. In other studies, a similar array of antiviral effects against mumps virus in tissue cultures were also found.

cation was administered orally, beginning 24 hours post-infection. Disease progression and drug effect were evaluated at 8 days by examination of the lung for pneumonic consolidation using the method of T. W. Chang and L. Weinstein (Am. J. Med. Sci., 1973, in press) and by the objective technic of weighing the lungs. Note that lung weight increase during influenza infection reflects edema, hemorrhage and virus content (see P. Gordon and E. R. Brown, Canad. J. Micro. 18:1463, 1972). Below in Table 3, part A, objective data are presented for lung weights illustrating an 82% suppression of disease by the derivative.

The above medication was also examined for its capacity to prevent death in mice ill with a lethal influenza A/PR/8 infection. The drug was given subcutaneously at 3 dose levels, once 90 minutes before infection. The results illustrate a significant dose-dependent protection against death and are shown in Table 3, part B.

TABLE 3

A. ACTION IN MICE ILL WITH INFLUENZA A$_2$/HONG KONG DISEASE

| Group | Average Lung Weight (mg) | % Disease Suppression | Frequency of Normal Lungs (<170 mg) |
|---|---|---|---|
| Normal | 160 | | 21/21 |
| Infected control | 258 | | 1/21 |
| Infected treated | 177 | 82 | 13/21 |

B. ACTION IN MICE ILL WITH A LETHAL INFLUENZA A/PR/8 INFECTION

| Drug | Mortality Frequency at 8 days | % Mortality | % of Population Protected |
|---|---|---|---|
| 0 (Control) | 42/44 | 95 | |
| 10 mg/Kg | 18/22 | 81 | 14 |
| 40 mg/Kg | 16/22 | 72 | 23 |
| 160 mg/Kg | 10/22 | 45 | 50 |

EXAMPLE 12

The most potent of the above derivatives, 3-O-3'-(N',N'-dimethylamino-n-propyl)-glucose, was examined for its capacity to suppress influenza A$_2$/Hong

I claim:

1. A compound selected from the group consisting of
3-O-3'-(N',N'-dimethylamino-n-propyl)-glucose,
3-O-4'-(N-methyl piperidyl)-glucose,
3-O-2'-(N',N'-dimethylaminoethyl)-glucose, 3-O-3'-(2',N',N'-trimethylamino-n-propyl)-glucose,
α-N,N-dimethylaminoisopropyl-glucoside,
6-O-3'-(N',N'-dimethylamino-n-propyl)-galactose,
3-O-2'-(N',N'-dimethylaminopropyl)-glucose,
6-O-2'-(N',N'-dimethylaminopropyl)-galactose, and therapeutically effective and acceptable organic acid and inorganic acid salts thereof.

2. A compound in accordance with claim 1 wherein the said compound is 3-O-3'-(N',N'-dimethylamino-n-propyl)-glucose.

3. A compound in accordance with claim 1 wherein the said compound is 3-O-4'-(N-methyl piperidyl)-glucose.

4. A compound in accordance with claim 1 wherein the said compound is 3-O-2'-(N',N'-dimethylaminoethyl)-glucose.

5. A compound in accordance with claim 1 wherein the said compound is 3-O-3'-(2',N',N'-trimethylamino-n-propyl)-glucose.

6. A compound in accordance with claim 1 wherein the said compound is α-N,N-dimethylaminoisopropyl-glucoside.

7. A compound in accordance with claim 1 wherein the said compound is 6-O-3'-(N',N'-dimethylamino-n-propyl)-galactose.

8. A compound in accordance with claim 1 wherein the said compound is 3-O-2'-(N',N'-dimethylaminopropyl)-glucose.

9. A compound in accordance with claim 1 wherein the said compound is 6-O-2'-(N',N'-dimethylaminopropyl)-galactose.

10. A compound selected from the group consisting of
3-O-3'-(N',N'-dimethylamino-n-propyl)-D-glucopyranose,
3-O-4'-(N-methyl piperidyl)-D-glucopyranose,
3-O-2'-(N',N'-dimethylaminoethyl)-D-glucopyranose,
3-O-3'-(2', N',N'-trimethylamino-n-propyl)-D-glucopyranose,
α-N,N-dimethylaminoisopropyl-D-glucoside,
6-O-3'-(N',N'-dimethylamino-n-propyl)-D-galactopyranose,
3-O-2'-(N',N'-dimethylaminopropyl)-D-glucopyranose,
6-O-2'-(N',N'-dimethylaminopropyl)-D-galactopyranose, and therapeutically effective and acceptable organic acid and inorganic acid salts thereof.

11. A compound in accordance with claim 10 wherein the said compound is 3-O-3'-(N',N'-dimethylamino-n-propyl)-D-glucopyranose.

12. A compound in accordance with claim 10 wherein the said compound is 3-O-4'-(N-methyl piperidyl)-D-glucopyranose.

13. A compound in accordance with claim 10 wherein the said compound is 3-O-2'-(N',N'-dimethylaminoethyl) D-glucopyranose.

14. A compound in accordance with claim 10 wherein the said compound is 3-O-3'-(2',N',N'-trimethylamino-n-propyl)-D-glucopyranose.

15. A compound in accordance with claim 10 wherein the said compound is α-N,N-dimethylaminoisopropyl-D-glucoside.

16. A compound in accordance with claim 10 wherein the said compound is 6-O-3'-(N',N'-dimethylamino-n-propyl)-D-galactopyranose.

17. A compound in accordance with claim 10 whrerein the said compound is 3-O-2'-(N',N'-dimethylaminopropyl)-D-glucopyranose.

18. A compound in accordance with claim 10 wherein the said compound is 6-O-2'-(N',N'-dimethylaminopropyl)-D-galactopyranose.

19. A compound in accordance with claim 1 wherein the compound is in the form of a salt of the said organic and inorganic acids, the said acids being selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acids, p-toluene sulfonic acid, lower alkyl monocarboxylic acids, oxalic acid, tartaric acid, lactic acid, pyruvic acid, malic acid, succinic acid, gluconic acid and glucuronic acid.

20. A compound in accordance with claim 10 wherein the compound is in the form of a salt of the said organic and inorganic acids, the said acids being selected from the group consisting of HCl, HBr, $H_2SO_4$, $HNO_3$, benzoic acid, p-aminobenzoic acid, p-acetamidobenzoic acid, p-hydroxybenzoic acid, alkane sulfonic acids, p-toluene sulfonic acid, lower alkyl monocarboxylic acids, oxalic acid, tartaric acid, lactic acid, pyruvic acid, malic acid, succinic acid, gluconic acid and glucuronic acid.

21. A compound in accordance with claim 19 wherein the said compound is 3-O-3'-(N',N'-dimethylamino-n-propyl)-glucose.

22. A compound in accordance with claim 21 wherein the said acid is HCl.

23. A compound in accordance with claim 20 wherein the said compound is 3-O-3'-(N',N'-dimethylamino-n-propyl)-D-glucopyranose.

24. A compound in accordance with claim 23 wherein the said acid is HCl.

* * * * *

UNITED STATES PATENT AND TRADEMARK OFFICE
CERTIFICATE OF CORRECTION

PATENT NO. : 3,939,145

DATED : February 17, 1976

INVENTOR(S) : PAUL GORDON

It is certified that error appears in the above-identified patent and that said Letters Patent are hereby corrected as shown below:

Column 4, line 67 under "3-O-D-glucose," the dash (-) should read a ditto mark ( " ).

Signed and Sealed this eighteenth Day of May 1976

[SEAL]

Attest:

RUTH C. MASON
Attesting Officer

C. MARSHALL DANN
Commissioner of Patents and Trademarks